United States Patent [19]

Sasaki et al.

[11] Patent Number: 5,165,919
[45] Date of Patent: Nov. 24, 1992

[54] MEDICAL MATERIAL CONTAINING COVALENTLY BOUND HEPARIN AND PROCESS FOR ITS PRODUCTION

[75] Inventors: Masatomi Sasaki; Shinichi Kaneda; Nobuyoshi Kashiwagi, all of Shizuoka, Japan

[73] Assignee: Terumo Kabushiki Kaisha, Tokyo, Japan

[21] Appl. No.: 582,185

[22] PCT Filed: Mar. 15, 1989

[86] PCT No.: PCT/JP90/00275
§ 371 Date: Sep. 26, 1990
§ 102(e) Date: Sep. 26, 1990

[87] PCT Pub. No.: WO89/09069
PCT Pub. Date: Oct. 5, 1989

[30] Foreign Application Priority Data

Mar. 28, 1988 [JP] Japan .................. 63-74088

[51] Int. Cl.$^5$ .................. A61K 31/725; A61L 33/00; B01D 71/82; D06M 15/03
[52] U.S. Cl. .................. 424/488; 424/78.18; 523/112; 525/54.2; 525/54.21; 525/54.23; 428/288; 428/311.7; 428/375; 428/378; 428/414; 428/420; 428/500; 428/507; 428/508; 428/515; 428/516; 428/517; 428/518; 210/646; 210/654; 210/655; 210/500.24; 604/93; 623/1
[58] Field of Search ............... 424/488, 78.17, 78.18, 424/486, 487; 523/105, 112; 525/54.2, 54.21, 54.23

[56] References Cited

U.S. PATENT DOCUMENTS 3,917,894 11/1975 Coleman ............... 428/414
4,248,736 2/1981 Fuchigami et al. ........ 210/646
4,859,758 8/1989 Shalati et al. ........... 527/314
4,863,907 9/1989 Sakurai et al. .......... 514/56

FOREIGN PATENT DOCUMENTS 3109141 9/1982 Fed. Rep. of Germany .
63-48336 3/1988 Japan .
WO88/4183 6/1988 World Int. Prop. O. .

Primary Examiner—Thurman K. Page
Assistant Examiner—E. J. Webman
Attorney, Agent, or Firm—Burns, Doane, Swecker & Mathis

[57] ABSTRACT

A medical material comprising a high-molecular weight material and a heparin derivative is provided, which high-molecular weight material comprises a high-molecular weight compound having functional groups capable of binding with epoxy groups, a compound having at least two amino groups and a polymer having a number of epoxy groups, said functional groups and some of said amino groups being bound to said epoxy groups, and which heparin derivative comprises heparin and an epoxy compound having at least two epoxy groups part of which is bound to amino groups in the heparin, the amino groups not bound to the epoxy groups in said high-molecular weight material being bound to the epoxy groups not bound to the amino groups in the heparin derivative. Also provided are an intermediate (high-molecular weight material) to be used for said medical material, as well as processes for producing said medical material and said intermediate. This medical material retains the activity of heparin intact and has it bound strongly and in a large amount. Further, this medical material has good biocompatibility. The above-described intermediate and processes for production further enhance the characteristics of the above-described medical material.

20 Claims, 2 Drawing Sheets

MEDICAL MATERIAL CONTAINING COVALENTLY BOUND HEPARIN AND PROCESS FOR ITS PRODUCTION

TECHNICAL FIELD

This invention relates to a medical material, particularly a medical material having high antithrombotic property, as well as an intermediate therefor and processes for producing said medical material and intermediate.

BACKGROUND ART

Many methods have heretofore been proposed for imparting biocompatibility to medical materials.

Regenerated cellulosic materials are used advantageously as medical polymer materials, and it is well known to obtain anticoagulant medical polymer materials by fixing heparin to regenerated cellulose or derivatives thereof.

However, this method of fixing heparin directly to the substrate cellulose has only limited practical feasibility on account of problems such as insufficient heparin fixation.

Many processes have therefore, been proposed for producing medical polymeric materials to solve these problems. An exemplary process consists of reacting a heparin derivative with a polymerizable vinyl monomer and regenerated cellulose or a derivative thereof in an aqueous solvent in the presence of a polymerization initiator to thereby impart anticoagulation to the regenerated cellulose (see, for example, Unexamined Published Japanese Patent Application No. 162702/1982).

DISCLOSURE OF INVENTION

However, none of the methods discovered to date satisfy the requirement for increased throughput of treatments which is a particularly important factor for the biocompatibility to be imparted to medical materials.

For instance, one possible method consists of introducing functional groups at the surface of a material to be treated. However, aligning them on the surface is not practically feasible because of the difficulty involved in the molding technique employed.

Another possible method consists of coating after molding but no coating materials that are capable of solving the problem of delamination have yet been developed.

A coating material could be used as a binder but this method has a problem to be solved in association with the alignability of functional groups.

There has also been proposed a method that increases the throughput of treatments by making use of functional groups in a molded part. The major problem with this method is that the molded part is adversely affected by severe reaction conditions for introducing the functional groups to a polymeric material forming the molded part.

The present invention been accomplished with the aforementioned problems taken into account and its object is to provide a medical material having particularly high antithrombotic property, as well as an intermediate therefor and processes for producing said medical material and intermediate by increasing the amount of functional groups on a high-molecular weight compound.

In order to attain this object, the present invention provides a high-molecular weight (polymer) material comprising a high-molecular weight (first polymer) compound having functional groups capable of binding with epoxy groups and a (second) polymer having a number of epoxy groups, said functional groups being bound to some of said epoxy groups, with the other epoxy groups remaining unreacted.

In accordance with the present invention, there is also provided a high-molecular weight (polymer) material comprising a high-molecular weight (first polymer) compound having functional groups capable of binding with epoxy groups, a compound having at least two amino groups and a (second) polymer having a number of epoxy groups, said functional groups and some of said amino groups being bound to said epoxy groups, with the other amino groups remaining unreacted.

Preferably, the above-described (second) polymer having epoxy groups has a vinyl monomer as an essential component and has at least three epoxy groups per unit chain length.

According to the present invention, there is further provided a medical material comprising a high-molecular weight (polymer) material and a heparin derivative, said high-molecular weight (polymer) material comprising a high-molecular weight (first polymer) compound having functional groups capable of binding with epoxy groups, a compound having at least two amino groups and a (second) polymer having a number of epoxy groups, said functional groups and some of said amino groups being bound to said epoxy groups, said heparin derivative comprising heparin and an epoxy compound having at least two epoxy groups part of which is bound to amino groups in the heparin, the amino groups not bound to the epoxy groups in said high-molecular weight (polymer) material being bound to the epoxy groups not bound to the amino groups in said heparin derivative.

Preferably, the above-described polymer having epoxy groups has a vinyl monomer as an essential component and has at least three epoxy groups per unit chain length.

It is also preferred that the aforementioned medical material is used as an antithrombotic material.

According to the present invention, there is also provided a process for producing a high-molecular weight (polymer) material comprising a high-molecular weight (first polymer) compound having functional groups capable of binding with epoxy groups and a (second) polymer having a number of epoxy groups, said functional groups being bound to some of said epoxy groups, with the other epoxy groups remaining unreacted, which process is characterized in that the above-described high-molecular weight (first polymer) compound is reacted with the above-described (second) polymer in an acetone-containing solution.

According to the present invention, there is further provided a process for producing a high-molecular weight (polymer) material comprising a high-molecular weight (first polymer) compound having functional groups capable of binding with epoxy groups, a compound having at least two amino groups and a (second) polymer having a number of epoxy groups, said functional groups and some of said amino groups being bound to said epoxy groups, with the other amino groups remaining unreacted, which process is characterized in that a high-molecular weight (polymer) material which is the product of reaction between the above-described high-molecular weight (first polymer) compound and the (second) polymer having a number of epoxy groups and in which the functional groups in the high-molecular weight (first polymer) compound that are capable of binding with epoxy groups are bound to some of the epoxy groups in the (second) polymer, with the other epoxy groups remaining unreacted in the reaction product, is reacted with the above-described compound having at least two amino groups in an aqueous solution.

According to the present invention, there is also provided a process for producing a medical material comprising a high-molecular weight (polymer) material and a heparin derivative, said high-molecular weight (polymer) material comprising a high-molecular weight (first polymer) compound having functional groups capable of binding with epoxy groups, a compound having at least two amino groups and a (second) polymer having a number of epoxy groups, said functional groups and some of said amino groups being bound to said epoxy groups, said heparin derivative comprising heparin and an epoxy compound having at least two epoxy groups part of which is bound to amino groups in the heparin, the amino groups not bound to the epoxy groups in said high-molecular weight (polymer) material being bound to the epoxy groups not bound to the amino groups in the heparin derivative, which process is characterized in that a heparin derivative having the amino groups in heparin bound to some of the epoxy groups in the epoxy compound, with the other epoxy groups remaining unreacted in the reaction product, is reacted with the above-described high-molecular weight (polymer) material in an aqueous solution.

BEST MODE FOR CARRYING OUT THE INVENTION

Figure 1:
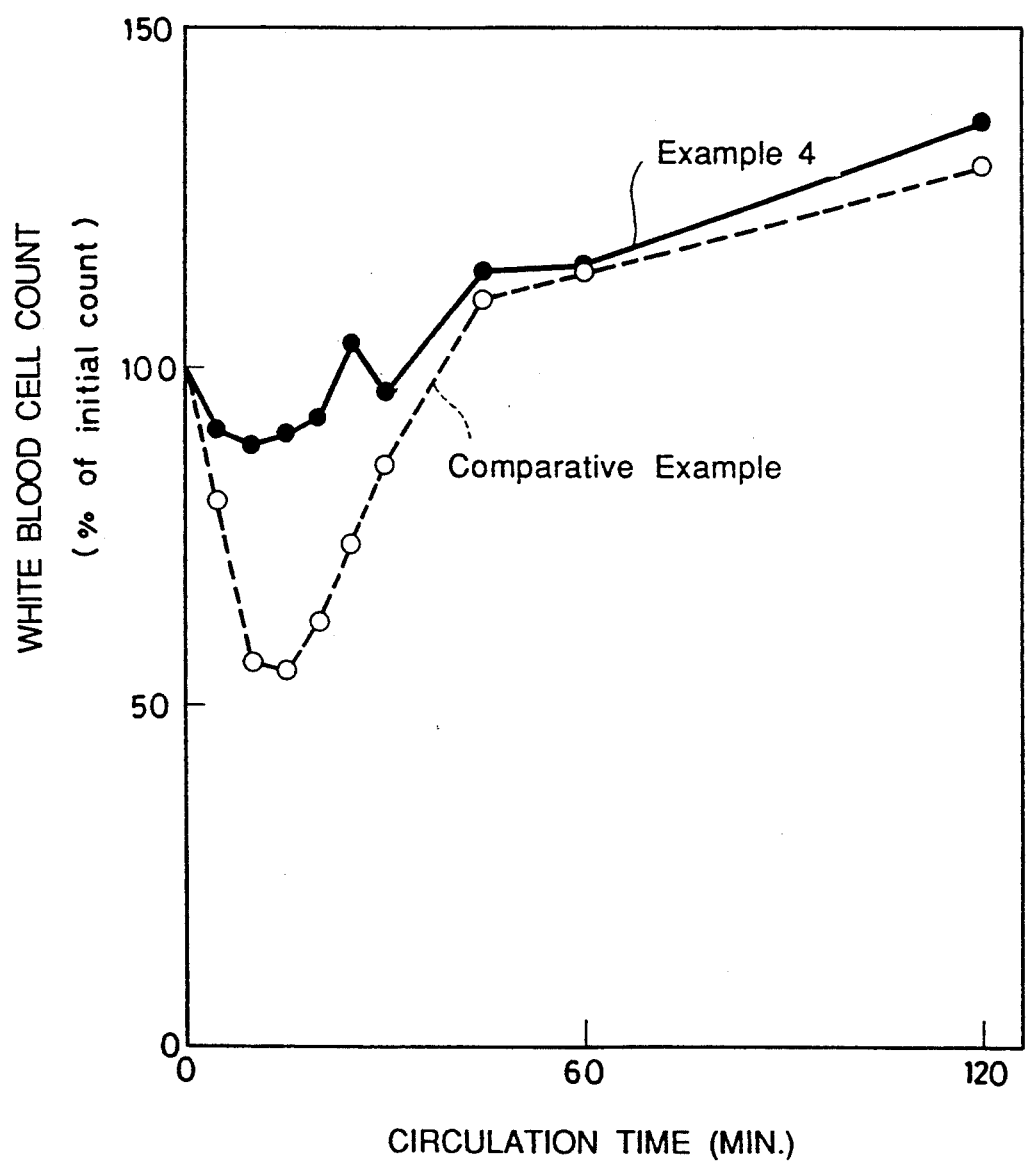
FIG. 1 is a graph showing the variation in the leukocyte count in an extracorporeal circulation experiment with rabbits.

The present invention will now be described below in greater detail.

The present invention includes three embodiments of compounds. The compound of the first embodiment is the combination (C) in which a high-molecular weight compound (A) having functional groups capable of binding with epoxy groups is bound to a polymer (B) having a number of epoxy groups.

The compound of the second embodiment is the combination (E) in which the combination (C) obtained in the first embodiment is bound to a compound (D) having at least two amino groups.

The compound of the third embodiment is the combination (G) in which the combination (E) obtained in the second embodiment is bound to a heparin derivative (F).

To begin with, the high-molecular weight materials of the present invention, namely, the aforementioned combinations (C) and (E) will now be described below.

The high-molecular weight compound (A) to be used in the present invention has one or more functional groups capable of binding with epoxy groups such as those selected from among hydroxyl groups, amino groups and carboxyl groups. Examples of (A) include regenerated cellulose, various cellulosic derivatives, polymethacrylic acid, polyhydroxyethyl methacrylate and copolymers thereof, chitosan, polyvinyl alcohol and ethylene vinyl-alcohol copolymer. Materials having good molding and processing properties can be obtained by using compounds having one or more of hydroxyl groups, amino groups and a carboxyl groups.

The polymer (B) to be used in the present invention preferably contains a vinyl monomer as an essential component in the skeleton and a linear polymer having either one of a methacrylic acid and an acrylic acid as an essential component is particularly preferred. The number of epoxy groups is preferably at least three per unit chain length and those which contain many epoxy groups are particularly preferred. However, in consideration of the conditions for synthesis of linear polymers, it is more preferred that epoxy groups are present in a weight ratio of 20–50% of glycidyl methacrylate in the case of acrylic acid containing polymers.

Further, it is preferred that components having those substances in side chains which have a volume displacement effect are incorporated in the skeleton of the linear polymer so that the molecular radius of its own molecule will increase to provide enhanced reactivity, and substances having a fluorine compound in side chains are particularly advantageous.

In accordance with a process for producing the high-molecular weight material (C) of the present invention, the above-described high-molecular weight compound (A) that is preliminarily immersed in a solution of an alkali such as sodium hydroxide, lithium hydroxide, potassium hydroxide or calcium hydroxide may be immersed in an acetone solution of the above-described polymer (B) at room temperature. When the high-molecular weight material (C) of the present invention is to be used as an intermediate for a highly antithrombotic medical material, heparin or a derivative thereof that have a hydroxyl group, an amino group, a carboxyl group, etc. may be directly bound to the high-molecular weight material (C) of the present invention but, if it is desired to enhance the effect of treatment of said high-molecular weight (C) with heparin or a derivative thereof, but in order to enhance the effect of treatments, a compound containing a number of such groups as hydroxyl, amino and carboxyl groups is preferably used as a binder. According to another method, catalysts may be used.

From this viewpoint, in the second embodiment of the present invention, there is provided the high-molecular weight material (E) in which a particularly highly reactive compound (D) having at least two amino groups and which is used as a binder is bound to the above-described high-molecular weight material (C). In producing the high-molecular weight material (E), compound (D) having at least two amino groups such as polyethyleneimine or polyacrylamide is used, so said amino groups will readily bind to those epoxy groups in the above-described polymer (B) which have not bound to the functional groups in the above-described high-molecular weight compound (A) which are capable of binding with epoxy groups, to thereby yield a high-molecular weight material (E) having an even enhanced effect of treatments.

In accordance with a process for producing the high-molecular weight material (E) of the present invention, the above-described high-molecular weight material (C) may be immersed in an aqueous solution of the above-described heparin derivative, to thereby yield a medical material in which the amino groups remaining unreacted in the high-molecular weight material are bound to the epoxy groups remaining unreacted in the heparin derivative. In this instance, the pH is preferably adjusted to lie within the range of 3.5-12.

The reaction time may vary with other reaction conditions such as pH and reaction temperature but it is usually within the range of from 1 minute to 24 hours. To take as an example the condition where the pH is 4.5 and the temperature is 45° C., the reaction time of from 30 minutes to 3 hours is particularly preferred.

The thus obtained medical material of the present invention retains the activity of heparin intact because it is produced under mild reaction conditions. Further, it has a strong and yet stable binding with the high-molecular weight material and hence is advantageously used as the constituent material of medical devices that contact blood such as artificial blood vessels and artificial organs (e.g. intravascular self-retaining catheters, blood filters and plasma separators).

The present invention is described hereinafter in a more specific way with reference to examples.

EXAMPLE 1

A glass polymerization tube was charged with 0.25 parts by weight of azobisisobutyronitrile as a polymerization initiator, 12.5 parts by weight of methyl methacrylate, 25 parts by weight of glycidyl methacrylate and 12.5 parts by weight of hexafluoroisopropyl methacrylate, and this polymerization tube was cooled in liquid nitrogen, degassed with a vacuum pump, purged with nitrogen, further degassed and thereafter sealed by fusion. The tube was heated at 60° C. in a thermostatic bath until the contents solidified. Thereafter, the tube was cooled and opened at an end, with the contents being dissolved in tetrahydrofuran and reprecipitated in methanol to thereby obtain a white linear polymer.

A regenerated cellulose membrane (0.3 g ; thickness, 0.2 mm) used as a high-molecular weight compound was immersed in an aqueous solution of 0.5 w/v % sodium hydroxide for 30 minutes and said cellulose membrane was further immersed in a 0.5 w/v % acetone solution of the above-described linear polymer, with reaction being carried out at room temperature for 24 hours. Subsequently, the cellulose membrane was recovered and washed thoroughly with an organic solvent, then with distilled water.

EXAMPLE 2

The cellulose membrane obtained in Example 1 was further immersed for 10 minutes in a 0.5 w/v % aqueous solution of polyethyleneimine (mol. wt. 70,000) that had been adjusted to a pH of 8 and the membrane was thereafter washed thoroughly.

Further, the above-described cellulose membrane was immersed in water and sterilized by autoclaving at 115° C. for 60 minutes to prepare a sample.

EXAMPLE 3

Polyethylene glycol diglycidyl ether (mol. wt. 1,110) was dissolved in an amount of 0.444 g ($4 \times 10^{-4}$ mol) in 10 ml of water. To the resulting solution, 1.0 g of heparin sodium was added and dissolved uniformly. Thereafter, the pH of the reaction solution was adjusted to 9.0 with a 0.1 N sodium hydroxide solution. The resulting solution was stirred for 5 days at room temperature to effect reaction and, further, the pH was adjusted to 7.0 with 0.1 N sulfuric acid. In order to remove the unreacted polyethylene glycol diglycidyl ether, 10 ml of chloroform was added and the mixture was stirred, followed by centrifugation at 3,200 r.p.m. for 30 minutes to recover an aqueous solution of heparin derivative. This extraction process was repeated two more times and, subsequently, the aqueous solution of heparin derivative was lightly evaporated and diluted with a predetermined amount of water to obtain an aqueous solution of heparin derivative.

In the next place, the pH of an aqueous solution of this heparin derivative was adjusted to 4.5 with 0.1 N sulfuric acid and the cellulose membrane obtained in Example 2 was immersed in a 0.2 w/v % aqueous solution of said heparin derivative at 45° C. for 3 hours. The so treated membrane of regenerated cellulose was recovered and washed thoroughly.

EXPERIMENT 1

Evaluation of the Treated Membrane of Regenerated Cellulose)

Using a polypropylene syringe containing 3.8 wt % sodium citrate which was one tenth the volume of the blood to be samples, the venous blood of a healthy human was sampled and transferred gently into a polypropylene test tube by allowing it to trickle down the tube wall. The test tube was then centrifuged at 800 r.p.m. for 5 minutes to sample the platelet rich plasma (PRP) in the supernatant, which was diluted with a 3.8 wt % sodium citrate diluent (1/10 the volume of 0.01 M phosphate buffered physiological saline PBS, pH 7.4)) to thereby prepare a platelet suspension containing 100,000 platelets per $mm^3$.

This platelet suspension (0.2 ml) was placed on each of the above-described treated membrane of regenerated cellulose (1 $cm^2$) and controls for comparison, i.e., an untreated membrane of regenerated cellulose, polymethyl methacrylate (PMMA) and polypropylene (PP), to give a thickness of 2 mm and held in contact for 30 minutes at room temperature. After the lapse of a predetermined time, each sample was lightly washed with a 3.8 wt % sodium citrate diluent and subsequently immersed in a 1.0 wt % glutaraldehyde/0.01 M phosphate buffered physiological saline (PBS, pH 7.4) at a cool place for 24 hours to be fixed. After being washed lightly with distilled water, each sample was dehydrated through stages with ethanol series (treated successively for 10 minutes with ethanol having a respective concentrations of 50 wt %, 60 wt %, 70 wt %, 80 wt %, 90 wt %, 95 wt % and 100 wt %), dried with air and examined under a scanning electron microscope (JSM-840 of JEOL Ltd.). The evaluation method consisted of counting the number of adherent platelets per 0.07 $mm^2$ and examining the morphological changes in the platelets. The morphological changes were classified into the following three types.

Type I : Turned spherical from the normal disk shape of platelets, with 3 or 4 pseudopodia protruding; the adhesion to the surface of the substrate material would be comparatively weak;

Type II : With at least several pseudopodia extending, cells spread to one half the length of the pseudopodia; the adhesion to the surface of the substrate material would be strong;

Type III: Thin cells which spread to more than one half the length of pseudopodia expanded almost completely to present pseudocircular form in appearance; the adhesion to the surface of the substrate material would be complete.

The test results are shown in Table 1.

TABLE 1

| Sample | Platelet form (%) | | | No. of adhering platelets per 0.07 m$^2$ |
|---|---|---|---|---|
| | Type I | Type II | Type III | |
| Example 3 | 87.0 | 13.0 | 0.0 | 23 |
| Untreated membrane of regenerated cellulose | 90.9 | 6.3 | 2.8 | 144 |
| PMMA | 22.6 | 22.5 | 54.9 | 685 |
| PP | 15.6 | 48.0 | 36.4 | 1001 |

EXPERIMENT 2

The above-described treated membrane of regenerated cellulose and untreated membrane of regenerated cellulose (control for comparison) were analyzed by X-ray photoelectron spectroscopy (ESCA: JPS 90SX of JEOL Ltd.) and the results of ESCA spectra for the individual atoms are shown in Table 2.

TABLE 2

| Sample | Relative number of atoms (%) | | | | |
|---|---|---|---|---|---|
| | fluorine | oxygen | nitrogen | carbon | sulfur |
| Example 3 | 0.2 | 30.2 | 8.1 | 58.1 | 3.4 |
| Untreated membrane of regenerated cellulose | 0.0 | 40.9 | 0.7 | 58.4 | 0.0 |

EXAMPLE 4

Preparation of Dialyzer

Cuprammonium regenerated cellulose hollow fibers (i.d.=ca. 200 μm; membrane thickness=12 μm) were put into a glass tube one end of which was connected to an aspirator, with the other end being immersed in a 0.5 w/v % aqueous solution of NaOH. Further, the aqueous solution of NaOH was loaded into said hollow fibers by means of suction with the aspirator. After the loading, the hollow fibers were left at room temperature for 30 minutes. Subsequently, the aqueous solution of NaOH was discharged from the aforementioned hollow fibers, and then a 0.5 w/v % acetone solution of the linear polymer used in Example 1 was loaded into the glass tube by the same procedure and left at room temperature for 24 hours. Thereafter, the 0.5 w/v % acetone solution of the above-mentioned linear polymer was discharged and the glass tube was washed with acetone and further washed thoroughly with distilled water, followed by drying with a draft at a temperature of 25° C. In order to insure complete drying, the tube was left overnight in an oven at 60° C.

Using 341 hollow cellulose fibers thus treated and a polyurethane resin potting agent, a dialyzer having an effective length of 14 cm and an intramembrane surface area of 300 c$^2$ was constructed. Further, a 0.5 w/v % aqueous solution of polyethyleneimine (adjusted to pH 8) was loaded into the dialyzer for 10 minutes and the dialyzer was thereafter washed thoroughly. Further, a 0.2 w/v % aqueous solution of the heparin derivative used in Example 3 (adjusted to pH 4.5) was loaded into the dialyzer at 45° C. for 3 hours. Thereafter, the dialyzer was washed thoroughly, loaded with distilled water and sterilized by autoclaving at 115° C. for 60 minutes, so as to complete the preparation of the dialyzer.

EXPERIMENT 3

Conditioning a Living Body

A rabbit was fixed in a supine position on a Kitajima type bench. Subsequently, the hair in the area to be operated was clipped with electric clippers and the clipped area was wiped clean with an ethanol-soaked cotton gauze. The rabbit was incised with scissors along the median line from the submandibular area up to the clavicle. Further, the fascia was cut open and the right (or left) common carotid artery was separated with care being taken not to damage the nerves, branched blood vessels and the surrounding tissues. Subsequently, the left (or right) facial vein was separated by a great depth with equal care being taken, and a self retaining catheter "Surflow" (the trademark of Terumo Kabushiki Kaisha) equipped with a rubber cap for simultaneous injection of two solutions and that was filled with 11 U/ml of a heparinized physiological saline solution was inserted into the vein and fixed by ligation. In a similar way, a catheter was inserted into the aforementioned artery and fixed by ligation.

CIRCULATION EXPERIMENT

Using the thus conditioned rabbit, an experiment was conducted both with the above-mentioned dialyzer and with a comparative dialyzer accommodating a membrane of untreated cuprammonium regenerated cellulose hollow fibers having the same membrane area. Stated more specifically, an experimental circuit and each of the dialyzers were preliminarily subjected to priming washing with 100 ml of a physiological saline solution and the circuit was connected to both the artery and vein sides of the conditioned rabbit, and an extracorporeal circulation experiment was conducted at a blood flow rate of 10 ml/min for 2 hours. A 1 ml blood sample was taken both immediately after the start of the circulation and at given intervals, i.e., after 5, 10, 15, 20, 25, 30, 45, 60 and 120 minutes, and each of the blood samples was treated to be anticoagulant with a 1.5 wt % EDTA-2Na physiological saline solution, followed by counting the number of blood cells with ELT-8 (product of Orth Instruments Corp.). The resulting white blood cell count (WBC), platelet count (PLT) and hematocrit count (HCT) are shown in Tables 3 and 4. Table 3 shows the data from the experimental circuit using the dialyzer accommodating the treated membrane of the cuprammonium regenerated cellulose hollow fibers obtained in Example 4, and FIG. 4 shows the data from the experimental circuit using the dialyzer accommodating the membrane of the untreated cuprammonium regenerated cellulose hollow fibers as a control for comparison. The white blood cell count and platelet count were corrected for Ht values and expressed in terms of values as reference against the Ht value immediately before the start of the circulation:

$$Cx = Co \times \frac{Htx}{Hto}$$

Cx: corrected value
Co: measured count
Htx: Ht value as reference for correction=initial Ht value
Hto: Ht value for the case where Co value was obtained.

TABLE 3

| TIME (min) | WBC MEAN (%) | WBC SD (%) | PLT MEAN (%) | PLT SD (%) | HCT MEAN (%) | HCT SD (%) |
|---|---|---|---|---|---|---|
| 0 | 100 | 0 | 100 | 0 | 100 | 0 |
| 5 | 90.2 | 7.8 | 96.4 | 3.9 | 99.9 | 1.9 |
| 10 | 88.9 | 20.3 | 95.2 | 7 | 100 | 2 |
| 15 | 90.3 | 19.1 | 97.2 | 2.3 | 100.3 | 2.5 |
| 20 | 92.8 | 17.3 | 95.8 | 4.5 | 100.8 | 3 |
| 25 | 103.9 | 12.1 | 92.7 | 4.9 | 100.5 | 2 |
| 30 | 96.9 | 16.9 | 91.8 | 4.4 | 100.6 | 2.2 |
| 45 | 115.2 | 5 | 89.8 | 3.4 | 99.9 | 2.1 |
| 60 | 116.4 | 15.5 | 89.7 | 14.4 | 99.1 | 2.9 |
| 120 | 138 | 16.6 | 87.8 | 14.8 | 97.9 | 3.5 |

TABLE 4

| TIME (min) | WBC MEAN (%) | WBC SD (%) | PLT MEAN (%) | PLT SD (%) | HCT MEAN (%) | HCT SD (%) |
|---|---|---|---|---|---|---|
| 0 | 100 | 0 | 100 | 0 | 100 | 0 |
| 5 | 80.7 | 11.6 | 97.8 | 14 | 99.9 | 1.1 |
| 10 | 56.5 | 6 | 91 | 15.7 | 100.2 | 1.8 |
| 15 | 55.6 | 7.5 | 87.3 | 17.6 | 100.4 | 2.3 |
| 20 | 62.6 | 10.5 | 84.3 | 16 | 100.8 | 2.1 |
| 25 | 74.5 | 15.5 | 80.2 | 15.3 | 99.4 | 3.2 |
| 30 | 86 | 21.1 | 77.2 | 17.7 | 99.3 | 2.7 |
| 45 | 111 | 31 | 70.2 | 13.4 | 97.3 | 5.2 |
| 60 | 115.5 | 21.5 | 58 | 16.2 | 97.3 | 3.3 |
| 120 | 131.9 | 23.8 | 44.7 | 12.1 | 95.3 | 4.9 |

Figure 2:
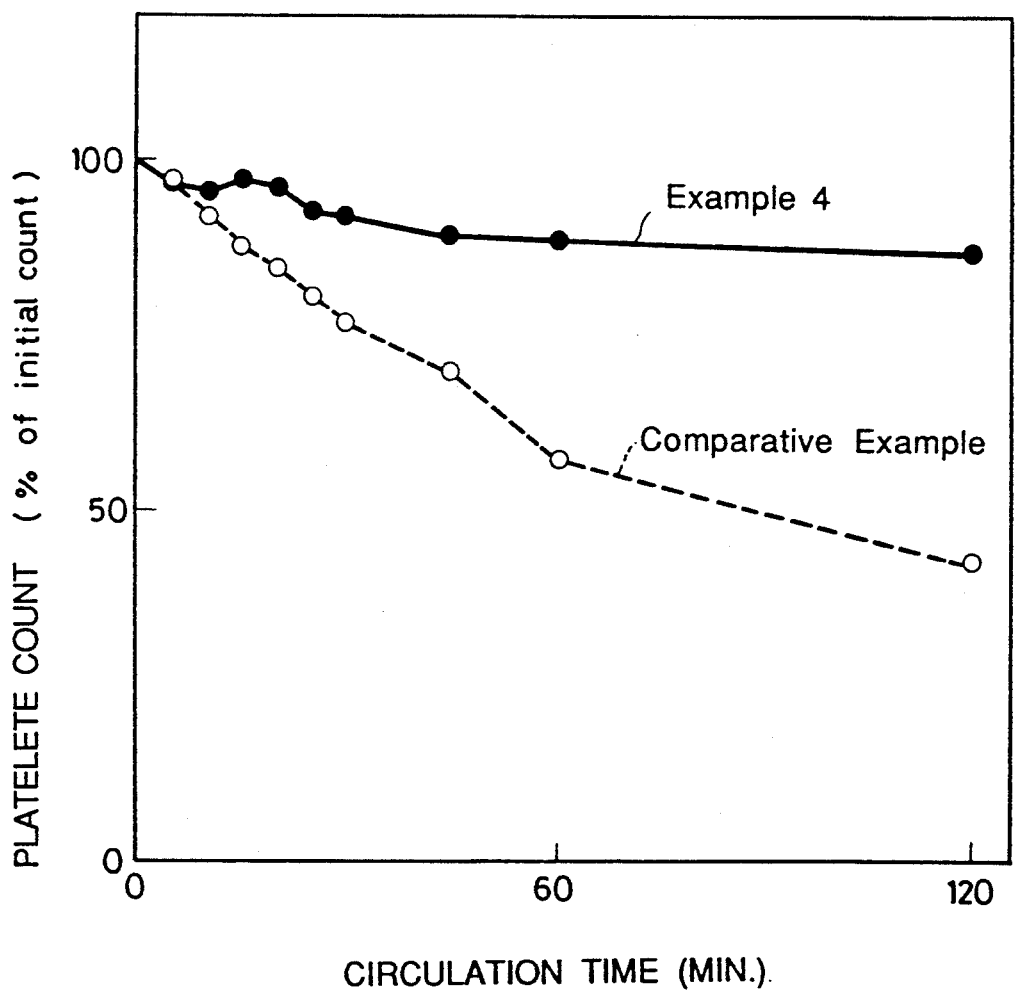
FIG. 2 is a graph showing the variation in the platelet count in the same experiment.

FIGS. 1 and 2 are graphs plotting the variations in the white blood cell count and platelet count that are shown in Tables 3 and 4, respectively; the solid lines refer to the data obtained with the dialyzer accommodating the membrane of the treated cuprammonium regenerated cellulose hollow fibers, and the dashed lines refer to the data obtained with the dialyzer accommodating the membrane of the untreated cuprammonium regenerated cellulose hollow fibers.

INDUSTRIAL APPLICABILITY

Having the constitution described above, the present invention offers the following advantages.

It is capable of providing a high-molecular weight material having an increased number of functional groups on a high-molecular weight compound and which can be used extensively as a material having improved molding and processing properties. This high-molecular weight material has many functional groups, so the throughput of subsequent treatments of substances is enhanced, whereby the effect of their treatment can be fully expected. Further, the reaction conditions for producing the medical material of the present invention need be comparatively mild so that possible effects on molding operations are sufficiently small to insure a comparatively advantageous handling property.

It is also capable of providing a medical material that retains the activity of heparin intact, that has a strong In addition, the process for the production of a medical material of the present invention is capable of not only permitting heparin to bind strongly to the high-molecular weight material but also providing a medical material, especially an antithrombotic material, that has biocompatibility and which intactly retains the anticoagulant activity of heparin.

What is claimed is:

1. A medical material which comprises a high-molecular weight material (E) and a heparin derivative (F), wherein said high-molecular weight material (E) comprises a polymer (A) having functional groups selected from the group consisting of hydroxyl groups, amino groups and carboxyl groups, a polymer (D), different from polymer A, having at least two amino groups and an epoxy group containing polymer (B) having a vinyl monomer as an essential component; said functional groups of the polymer (A) and some of said amino groups of the polymer (D) have reacted with the epoxy groups of the polymer (B); said heparin derivative (F) comprises heparin and a polymer (H) having two glycidyl groups per one polymer chain; some of the epoxy groups of said polymer (H) have reacted with amino groups int he heparin; and the amino groups remaining unreacted in said high-molecular weight material (E) have reacted with the epoxy groups remaining unreacted in the heparin derivative (F).

2. A medical material according to claim 1, wherein the polymer (B) having epoxy groups has at least three epoxy groups per unit chain length.

3. A medical material according to claim 1, wherein the polymer (D) is polyethyleneimine or polyacrylamide.

4. A medical material according to claim 1, wherein polymer (H) is polyethyleneglycol diglycidyl ether.

5. A process for producing the medical material of claim 1, which comprises reacting unreacted epoxy groups of a heparin derivative (F) with unreacted amino groups of a high-molecular weight material (E) in an aqueous solution, wherein said heparin derivative (F) comprises heparin and a polymer (H) having two diglycidyl groups per one polymer chain; some of the epoxy groups of said polymer (H) have reacted with amino groups in the heparin; said high-molecular weight material (E) comprises a polymer (A) having functional groups selected from the group consisting of hydroxyl groups, amino groups and carboxyl groups, a polymer (D), different form polymer A, having at least two amino groups and an epoxy group containing polymer (B) having a vinyl monomer as an essential component; and the functional groups of the polymer (A) and some of the amino groups of the polymer (D) have reacted with the epoxy groups of the polymer (B).

6. A process according to claim 5 wherein the epoxy group containing polymer (B) has at least three epoxy groups per unit chain length.

7. A process according to claim 5, wherein the polymer (D) is polyethyleneimine or polyacrylamide.

8. A process according to claim 6, wherein polymer (H) is polyethyleneglycol diglycidyl ether.

9. An antithrombotic material which comprises a high-molecular weight material (E) and a heparin derivative (F), wherein said high-molecular weight material (E) comprises a polymer (A) having functional groups selected from the group consisting of hydroxyl groups, amino groups and carboxyl groups, a polymer (D), different from polymer A, having at least two amino groups and an epoxy group containing polymer (B) having a vinyl monomer as an essential component; said functional groups of the polymer (A) and some of the amino groups of the polymer (D) have reacted with the epoxy groups of the polymer (B); said heparin derivative (F) comprises heparin and a polymer (H) having two glycidyl groups per one polymer chain; some of the epoxy groups of said polymer (H) have reacted with amino groups in the heparin; and the amino groups remaining unreacted in said high-molecular weight material (E) have reacted with the epoxy groups remaining unreacted in the heparin derivative (F).

10. An antithrombotic material according to claim 9, wherein the epoxy group containing polymer (B) has at least three epoxy groups per unit chain length.

11. An antithrombotic material according to claim 9, wherein the polymer (D) is polyethyleneimine or polyacrylamide.

12. An antithrombotic material according to claim 9, wherein polymer (H) is polyethyleneglycol diglycidyl ether.

13. A medical material obtained by reacting unreacted amino groups of a high-molecular weight material (E) with unreacted epoxy groups of a heparin derivative (F), wherein the high-molecular weight material (E) is obtained by reacting a reaction product containing unreacted epoxy groups which is obtained by reacting a polymer (A) having functional groups selected from the group consisting of hydroxyl groups, amino groups and carboxyl groups with an epoxy group containing polymer (B) having a vinyl monomer as an essential component, with a polymer (D), different from polymer A, having at least two amino groups, and wherein said heparin derivative (F) is obtained by reacting heparin with a polymer (H) having two diglycidyl groups per one polymer chain wherein some of the epoxy groups of the polymer (H) remain unreacted.

14. A medical material according to claim 13, wherein the epoxy group containing polymer (B) has at least three epoxy groups per unit chain length.

15. A medical material according to claim 13, wherein the polymer (D) is polyethyleneimine or polyacrylamide.

16. A medical material according to claim 13, wherein polymer (H) is polyethyleneglycol diglycidyl ether.

17. A process for producing a medical material, which comprises reacting unreacted amino groups of a high-molecular weight material (E) with unreacted epoxy groups of a heparin derivative (F), wherein said high-molecular weight material (E) is obtained by reacting a reaction product containing unreacted epoxy groups which is obtained by reacting a polymer (A) having functional groups selected from the group consisting of hydroxyl groups, amino groups and carboxyl groups with an epoxy group containing polymer (B) having a vinyl monomer as an essential component, with a polymer (D), different from polymer A, having at least two amino groups, and wherein said heparin derivative (F) is obtained by reacting heparin with a polymer (H) having two diglycidyl groups per one polymer chain wherein some of the epoxy groups of the polymer (H) remain unreacted.

18. A process according to claim 17, wherein the epoxy group containing polymer (B) has at least three epoxy groups per unit chain length.

19. A process according to claim 17, wherein the polymer (D) is polyethyleneimine or polyacrylamide.

20. A process according to claim 17, wherein polymer (H) is polyethyleneglycol diglycidyl ether.

* * * * *

UNITED STATES PATENT AND TRADEMARK OFFICE
CERTIFICATE OF CORRECTION

PATENT NO. : 5,165,919
DATED : November 24, 1992
INVENTOR(S) : Masatomi SASAKI et al It is certified that error appears in the above-indentified patent and that said Letters Patent is hereby corrected as shown below:

On the title page, Item [86]:

delete "PCT/JP90/00275" and insert -- PCT/JP89/00275 --.

In Column 1, line 61, after "invention", insert -- has --.

In Column 4, line 6, delete "a".

In Column 6, line 18, delete "Evaluation" and insert -- (Evaluation --.

In Column 9, line 53, delete "mold:ng" and insert -- molding --.

In Column 9, line 57, after "strong", insert -- binding to the high-molecular weight material, with said binding being a large amount and stable, and that has good biocompatability. Hence, said medical material can be extensively used as an antithrombotic material. --.

In Column 10, line 13, delete "int he" and insert -- in the --.

In Column 10, line 38, delete "form" and insert -- from --.

Signed and Sealed this

Fourth Day of January, 1994

*Attest:*

BRUCE LEHMAN

*Attesting Officer*   *Commissioner of Patents and Trademarks*